US009334386B2

(12) United States Patent
Alsharaeh et al.

(10) Patent No.: US 9,334,386 B2
(45) Date of Patent: May 10, 2016

(54) ANTIMICROBIAL POLYMER-GRAPHENE-SILVER NANOCOMPOSITE (71) Applicants: Edreese Housni Alsharaeh, Riyadh (SA); Mohammad Ateeq Aldosari, Riyadh (SA); Ali Abdel-Rahman Mohammad Othman, Riyadh (SA); Mohammed Faour Qasem Al-Hindawi, Riyadh (SA); Khaled Bin Bandar Alsaud, Riyadh (SA)

(72) Inventors: Edreese Housni Alsharaeh, Riyadh (SA); Mohammad Ateeq Aldosari, Riyadh (SA); Ali Abdel-Rahman Mohammad Othman, Riyadh (SA); Mohammed Faour Qasem Al-Hindawi, Riyadh (SA); Khaled Bin Bandar Alsaud, Riyadh (SA)

(73) Assignee: Alfaisal University, Riyadh (SA)

( * ) Notice: Subject to any disclaimer, the term of this patent is extended or adjusted under 35 U.S.C. 154(b) by 0 days.

(21) Appl. No.: 14/181,698

(22) Filed: Feb. 16, 2014

(65) Prior Publication Data

US 2015/0065601 A1  Mar. 5, 2015

Related U.S. Application Data (63) Continuation-in-part of application No. 14/017,645, filed on Sep. 4, 2013.

(51) Int. Cl.
*C08K 3/28* (2006.01)
*A61L 31/10* (2006.01)
(Continued)

(52) U.S. Cl.
CPC ............... *C08K 3/28* (2013.01); *A61L 24/0015* (2013.01); *A61L 24/0073* (2013.01); *A61L 31/10* (2013.01); *C08F 292/00* (2013.01); *C08K 3/04* (2013.01); *C09D 133/12* (2013.01); *A61L 2420/04* (2013.01); *A61L 2420/06* (2013.01); *B82Y 30/00* (2013.01); *B82Y 40/00* (2013.01)

(58) Field of Classification Search
CPC .......... B82Y 30/00; B82Y 40/00; C09D 1/00; C08K 3/04; C08K 2201/011; C01B 2204/02
See application file for complete search history.

(56) References Cited

U.S. PATENT DOCUMENTS 4,534,887 A * 8/1985 Broady et al. ................ 252/503
7,902,275 B2 * 3/2011 Gerhardt et al. ................ 524/1
(Continued)

FOREIGN PATENT DOCUMENTS

WO   WO 2011/119961   * 9/2011

OTHER PUBLICATIONS

Xu et al. J. Mater. Chem. 2011, 21, pp. 4593-4597.*
(Continued)

*Primary Examiner* — Michael A Salvitti
(74) *Attorney, Agent, or Firm* — Geeta Kadambi Riddhi IP LLC (57) ABSTRACT

The copolymer of styrene and methylmethacrylate containing reduced graphene oxide/silver nanoparticles (PS-PMMA/RGO/AgNPs) nanocomposite were prepared via in situ bulk polymerization method using two different preparation techniques. In the first approach, a mixture of graphene oxide (GO), styrene (S) and methylmethacrylate monomers (MMA) were polymerized using a bulk polymerization method with a free radical initiator. After the addition silver nitrate ($AgNO_3$), the product was reduced via microwave irradiation (MWI) in presence of the reducing agent hydrazine hydrate (HH), to obtain R-(GO-(PS-PMMA))/AgNPs nanocomposite. This nanocomposite was then used to create a material that had antimicrobial properties to be used in medical devices or medical related implants.

5 Claims, 11 Drawing Sheets (51) Int. Cl.
*C09D 133/12* (2006.01)
*A61L 24/00* (2006.01)
*C08K 3/04* (2006.01)
*C08F 292/00* (2006.01)
*B82Y 30/00* (2011.01)
*B82Y 40/00* (2011.01)

(56) References Cited

U.S. PATENT DOCUMENTS

| | | | | |
|---|---|---|---|---|
| 8,167,190 | B1* | 5/2012 | Bullock et al. | 228/119 |
| 8,222,321 | B2* | 7/2012 | Youm et al. | 523/215 |
| 8,557,916 | B1* | 10/2013 | Alsharaeh et al. | 524/700 |
| 8,871,171 | B2* | 10/2014 | El-Shall et al. | 423/445 B |
| 2010/0189901 | A1* | 7/2010 | Chung et al. | 427/256 |
| 2010/0276645 | A1* | 11/2010 | Aspin et al. | 252/513 |
| 2011/0104496 | A1* | 5/2011 | Cook et al. | 428/404 |
| 2011/0127471 | A1* | 6/2011 | Shin et al. | 252/506 |
| 2011/0160372 | A1* | 6/2011 | Youm et al. | 524/403 |
| 2011/0217544 | A1* | 9/2011 | Young et al. | 428/327 |
| 2011/0223480 | A1* | 9/2011 | Wee et al. | 429/218.1 |
| 2013/0123415 | A1* | 5/2013 | Tanaka et al. | 524/529 |
| 2013/0146821 | A1* | 6/2013 | Meyer et al. | 252/511 |
| 2013/0211106 | A1* | 8/2013 | El-Shall et al. | 549/445 |
| 2014/0048738 | A1* | 2/2014 | Xia et al. | 252/62.54 |
| 2014/0054490 | A1* | 2/2014 | Sundara et al. | 252/62.56 |
| 2015/0065601 | A1* | 3/2015 | Alsharaeh et al. | 522/81 |

OTHER PUBLICATIONS

Fang et al. Colloidal Polym. Sci. (2014) 292:985-990. Published online Jan. 5, 2014.*

Alsharaed et al. Polymer Composites (2014) pp. 2014-2323. Published online Jan. 27, 2014.*

Tan et al. Polym. Chem., 2013, 4, pp. 2939-2944. Published online Mar. 25, 2013.*

Tan et al. Supplementary Information for Polym. Chem., 2013, 4, pp. 2939-2944.*

* cited by examiner

ANTIMICROBIAL POLYMER-GRAPHENE-SILVER NANOCOMPOSITE

CROSS REFERENCE TO RELATED APPLICATION

This application is a continuation-in-part application and claims priority to U.S. patent application Ser. No. 14/017,645 filed on 4th September 2013. The pending U.S. application Ser. No. 14/017,645 is hereby incorporated by reference in its entireties for all of its teachings.

FIELD OF TECHNOLOGY

The present disclosure relates to a novel composition for a nanocomposite containing graphene sheets, monomer making polymers and metal nitrate as an antimicrobial agent. More specifically composition and method of making polymer nanocomposite containing graphene oxide with silver nanoparticles having antimicrobial properties.

BACKGROUND

An antimicrobial polymer system is a material that modified in purpose to inhibit bacterial growth. It is consist of a polymer matrix and an antimicrobial agent. There are wide spectrum applications for antimicrobial polymer such as in medicine, and personal hygiene industry (Vladimir Sedlarik, 2013). Any modification process in antibacterial polymer should consider the chemical and physical properties of the polymer, the toxicity, and thermal stability of the polymer. Moreover, technological factors such as functionality, and reproducibility should consider as well (Vladimir Sedlarik, 2013). One method of antimicrobial polymer preparation is the direct deposition of antimicrobial agent on a polymer surface. This method is simple, and widely used in medical devices (Vladimir Sedlarik, 2013).

Recently, silver nanoparticles as well as various silver-based compounds containing ionic silver ($Ag^+$) or metallic silver)($Ag^0$) exhibiting antimicrobial activity have been synthesized. Antibacterial activity of the silver-containing materials can be used, for example, in medicine to reduce infections in burn treatment and arthroplasty, as well as to prevent bacteria colonization on prostheses, dental materials, and bone cements. Silver-containing materials can be employed to eliminate microorganisms on textile fabrics, or they can be used for water treatment (Vladimir Sedlarik, 2013, Panáček, A., et al. 2006). However, one of many challenges is they all are coating based technology and do wear off over use. There is a need to find a more permanent solution so that the antimicrobial property of the material can be maintained for a long time. There is a need to find an optimal method to create a nanocomposite that has superior physical and chemical properties and is easy to make.

SUMMARY

The present disclosure describes an antimicrobial nanocomposite composition and its use for various industrial uses. In one embodiment, a composition for a nanocomposite having graphene sheet is described. In another embodiment, adding silver nitrate to the nanocomposite to make an antimicrobial nanocomposite composition to be used for medical devices and others.

In one embodiment, the nanocomposite comprises of silver nitrate, graphene, styrene and methyl methacrylate. In one embodiment, the nanocomposite is used for medical devices/ articles such as coating medical device, tubes and articles that are exposed to bacterial contamination exposure for long duration, bone cement, dentures, paper, paint and automotive article. In another embodiment, the nanocomposite has a superior nanomechanical properties compared to non MWI method of preparation.

In one embodiment, a method of making nanocomposite is by synthesizing reduced graphene oxide powder. In another embodiment, styrene and methyl methacrylate is mixed in a specific weight ratio. The ratio is 1:1. In another embodiment, specific time and specific temperatures are used for performing various steps to obtain a STY-co-MMA polymer with graphene sheets that is called a nanocomposite in the instant invention. The nanocomposite, in one embodiment, is made by using microwave irradiation (MWI).

The composition of the nanocomposite and using the nanocomposite disclosed herein may be implemented in any means for achieving various aspects, and may be executed to be used for various industrial applications including medical and non-medical applications. Other features will be apparent from the accompanying drawings and from the detailed description that follows.

BRIEF DESCRIPTION OF FIGURES

FIGS. 3. (a), (b), (c), (d), (f) (e) C1s and Ag3d XPS spectra of RGO/AgNPs/(PS-PMMA) nanocomposite.

Other features of the present embodiments will be apparent from the accompanying drawings and from the detailed description that follows.

DETAILED DESCRIPTION

In the instant invention the composition and preparation of the nanocomposite (using in situ and microwave method), characterization and evaluation of the chemical, structural properties, thermal behavior and intercalation and/or exfoliation, dispersion of graphene (GR) sheet is described. The instant disclosure reveals a combination of graphene sheets with monomers that may be combined to make polymers and silver nitrate ($AgNO_3$) being added as a antibacterial agent to create a nanocomposite that may be used for prevention of bacterial infection due to exposure to bacteria rich atmosphere such as medical facility and medical equipment's.

Several monomers such as ethylene, propylene, styrene, methyl methacrylate, vinyl chloride, Ethylene terephthalate, Dimethylsiloxane and tetraflouroethylene may be used. These may be used in combination and not the same may be used to make a polymer. By keeping two different monomer to make a polymer will help create a much stronger and effective coating capability polymer to coat medical devices.

Materials and Methods

Extra pure graphite powder (>99.5%), silver nitrate ($AgNO_3$), potassium permanganate ($KMNO_4$, >99%) and hydrogen peroxide ($H_2O_2$, 30%) were obtained from Merck, and hydrazine hydrate (HH, 80%) was obtained from Loba Chemi. Pvt. Ltd. Styrene (S) and Methyl methacrylate (MMA) monomers (Acros Chemical Co., 99%) were kept in a refrigerator and used as received. Benzoyl peroxide (BP) (BDH Chemicals Ltd.) was used as an initiator. Other solvents and chemicals were of analytical grade and used without further purification.

Preparation of Reduced Graphene Oxide/Silver Nanoparticles (RGO/AgNPs):

400 mg of graphene oxide (GO) was prepared by suspending in 25 ml of $H_2O$. The suspension was then sonicated for 30 minutes (Hummer et. al. 1958). Then 80 mg (20% (w/w)) of silver nitrate was added and the solution stirred for 30 minutes. Then the solution was placed inside a conventional microwave oven (Kenwood MW740) after adding 40 μl of the reducing agent (HH). The microwave oven (Kenwood MW740) was then operated at full power (900 W), in 30 s cycles (on for 10 s, off and stirring for 20 s) for a total reaction time of 1.2 minutes (Hassan et. al. 2009). Then centrifugation using a Centurion Scientific Ltd. centrifuge operated at 5000 rpm for 15 min and dried overnight at 80° C. Silver nanoparticles were prepared via similar procedure, in the absence of the RGO and GO.

In Situ Preparation of RGO/AgNPs-(PS-PMMA) Nanocomposite:

A mixture of specific weight ratio (1:1 wt %) of S/MMA, 2.0 (weight/weight %) of RGO/AgNPs, and 5.0% of BP initiator was sonicated for 1 hour. and then, the mixture were maintained at 60° C. for 20 h to promote in situ free radical bulk polymerization. After the polymerization was completed, the product was poured into an excess of methanol, washed with hot water several times, and dried in an oven at 80° C. overnight. For comparison, the neat PS-PMMA was prepared via a similar procedure in the absence of the Ag nano particles (NPs) and GO. This RGO/AgNPs-(PS-PMMA) nanocomposite nomenclature basically means this nanocomposite was not subjected to microwave irradiation.

Preparation of R-(GO-(PS-PMMA))/AgNPs Nanocomposite:

A mixture of (1:1 wt %) of S/MMA, 2.0 (wt/wt %) of GO, and 5.0% of BP was sonicated for 1 hour, and then, the mixture were maintained at 60° C. for 20 h to promote in situ free radical bulk polymerization to produce GO/PS-PMMA composites. Then, a mixture of 0.40 g of (GO/PS-PMMA), 40 μl of HH, and 0.08 g of $AgNO_3$ was sonicated for 1 hour and then the mixture were Reduced using MWI to obtain the final product R-(GO-(PS-PMMA))/AgNPs nanocomposite. This R-(GO-(PS-PMMA))/AgNPs nanocomposite nomenclature basically means the nanocomposite was subjected to microwave irradiation.

Antimicrobial Activity detection: The antimicrobial susceptibility test was conducted in nutrient agar by the disk-diffusion test (Kirby-bauer method). E. coli HB 101 K-12 previously stored in −50° C., was grown overnight in nutrient broth at 37° C. with shaking. 0.1 ml of E. coli HB 101 K-12 was spread on nutrient agar plates, and then equal weights (100 mg) of the samples were placed on the center of nutrient agar plate with gently press. After 24 hours of incubation at 37° C., colonies were detected, and the diameter of the inhibition zone was measured.

Chemical Characterization of the nanocomposite: The FTIR (Thermo Scientific Nicolet-iS10) spectra of the nanocomposite were recorded in the range of 4000-500 $cm^{-1}$. X-ray diffraction (Philips-Holland, PW 1729) of the nanocomposite were investigated with Cu radiation (30 kV, 40 mA, Kα radiation (λ=1.54430 Å)) between 28 of 5° and 100°. The XPS measurements were carried out by using a SPECS GmbH X-ray photoelectron spectrometer. Prior to analysis, the samples were degassed under vacuum inside the load lock for 16 h. The Raman spectra of nanocomposite were measured with a Bruker Equinox 55 FT-IR spectrometer equipped with an FRA106/S FT-Raman module and a liquid N2-cooled Ge detector using the 1064 nm line of a Nd:YAG laser with an output laser power of 200 mW. A scanning electron microscope (SEM, FEI Quanta 200, FEI, Hillsboro, USA) was employed to study the morphology of the nanocomposite after they were mounted on the nanocomposite slabs and coated with gold via sputtering system (Polaron E6100, Bio-Rad, UK). High resolution transmission electron microscopy (HRTEM) was carried out by using (JEOL JSM-2100F, Japan) and was operated at 200 kV. A drop of the composite dispersed in ethanol was placed on copper grids and dried for studies. The thermogravimetric analyses (TGA) of the nanocomposite were performed under an $N_2$ atmosphere at a heating rate of 10° C. per minute from 25° C. to 800° C. using a NETZCH 209 F1 thermogravimetric analyzer. Differential scanning calorimetry (DSC, NETZCH 204 F1) measurements were employed to estimate the glass-transition temperature ($T_g$) of each nanocomposite. The nanocomposites were heated from −25° C. to 100° C. at a heating rate of 10° C. per min. Then, a double run was performed after cooling at a heating rate of 2° C. per min from 25° C. to 350° C. The $T_g$ was taken as the midpoint of the transition.

Figure 1:
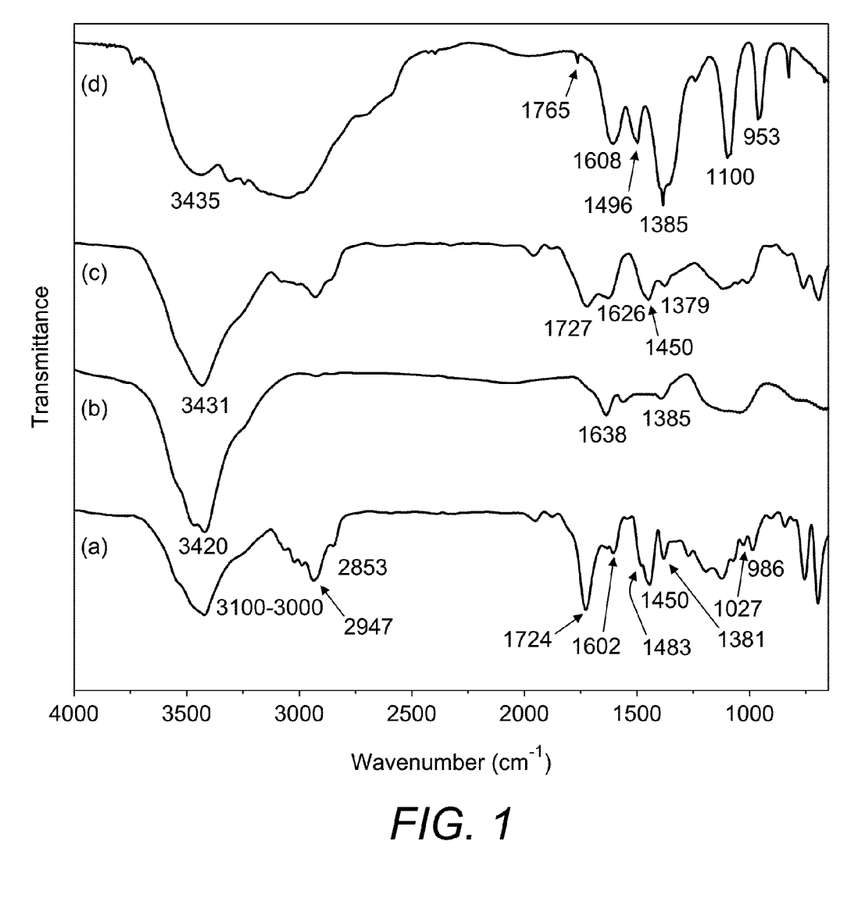
FIG. 1. FTIR spectra of (a) PS-PMMA, (b) RGO/AgNPs, (c) RGO/AgNPs-(PS-PMMA), and (d) R-(GO-(PS-PMMA))/AgNPs nanocomposite.

Results and Discussion:

FTIR spectral analysis was performed to confirm the chemical structure of all RGO/AgNPs-copolymers composites. FIG. 1 shows the FTIR spectra of neat PS-PMMA, RGO/AgNPs, RGO/AgNPs-(PS-PMMA), and R-(GO-(PS-PMMA))/AgNPs nanocomposite. The FTIR spectrum of the neat PS-PMMA (a), shows the typical characteristic bands (Alshareah et. al. 2013) at 3000-3100, 2947 and 2853, and 1680-2000, 1602, 1483, 1450, and 1027 $cm^{-1}$ which correspond to Ar—H and =C—H stretching, the aliphatic C—H and —$CH_2$, and aromatic C=C stretching, respectively, in the PS molecules. While the characteristic bands at 1724, and 1160-1120 $cm^{-1}$ which correspond to C=O stretching vibrations of ester carbonyl, and C—O—C stretching vibrations, respectively, in the PMMA molecules. The FTIR spectrum of RGO/AgNPs (b) shows bands at 3420, and 1638 $cm^{-1}$ that correspond to O—H and C=C groups, respectively. In the case of RGO/AgNPs-(PS-PMMA) nanocomposite (c), the spectrum shows presence of bands at 3431, 1727, 1170-1114, and 1626 and 1450 $cm^{-1}$ that correspond with the O—H, C=O and C—O—C, and C=C groups, respectively. This may suggest a successful intercalation of RGO/AgNPs within PS-PMMA copolymer matrix. Interestingly, for R-(GO-(PS-PMMA))/AgNPs, (d) the spectrum shows that these characteristics peaks are enhanced in intensity and much shifted to 3435 and 1765 $cm^{-1}$ in comparison with (c) when the microwave was not used, this may suggest that this enhancement in the intensity of aromatics of (S) and ester (MMA) regions is due to π-π stacking and acrylate interaction between RGO and polymer matrix. In addition, (d) shows that in the aromatic overtones (at 1680 to 2000 cm$^{-1}$), the aliphatic C—H, and —CH$_2$ (at 2950, 2853 cm$^{-1}$), and aromatic C=C stretching (1608 cm$^{-1}$) regions, the bands were broadened in comparison to (c). Moreover, the absence of band at 1724 cm$^{-1}$ in case of MWI nanocomposite (d), the disappearance of bands at 1483, 1450 and 1027 cm$^{-1}$ and the appearance of only one strong band at 1385 cm$^{-1}$ may be attributed to the contribution the stabilization of the AgNPs by the acrylate, C=C and O—H bonds (Y. N. Rao et. al. 2010). Overall, the FTIR results may suggest that MWI induces more electron chain transfer sites, and therefore will promote more interfacial interactions between RGO/AgNPs within PS-PMMA matrix.

Figure 2:
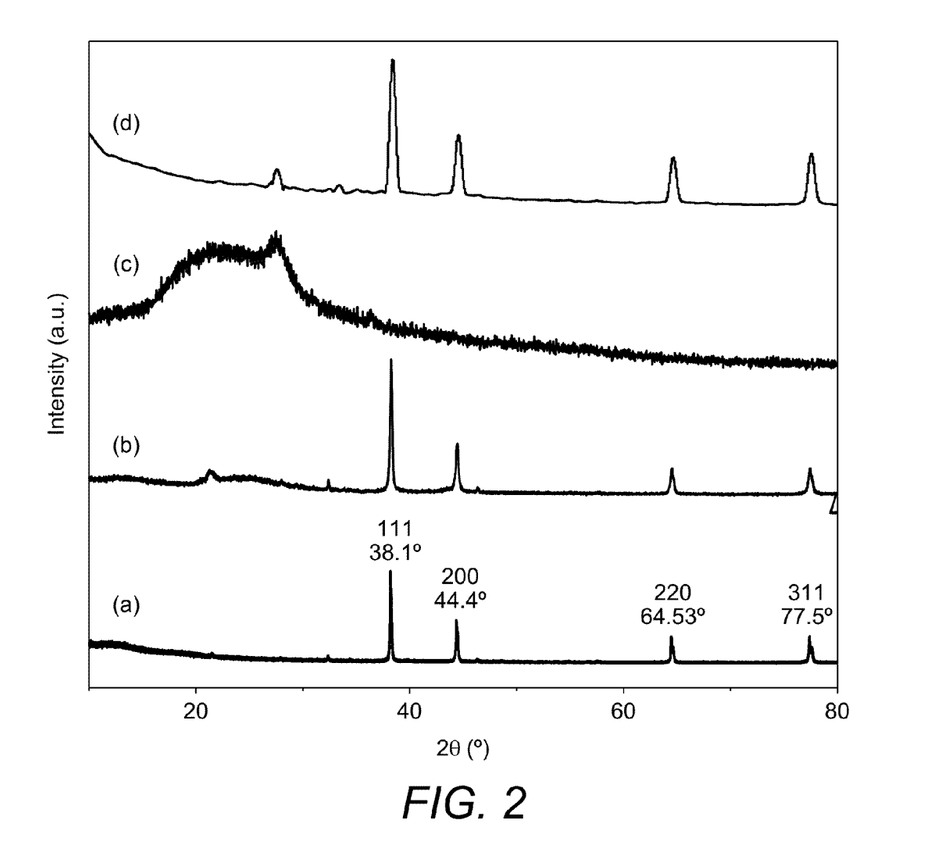
FIG. 2. XRD patterns of (a) AgNPs, (b) RGO/AgNPs, (c) RGO/AgNPs-(PS-PMMA), and (d) R-(GO-(PS-PMMA))/AgNPs nanocomposite.
Figure 3A:
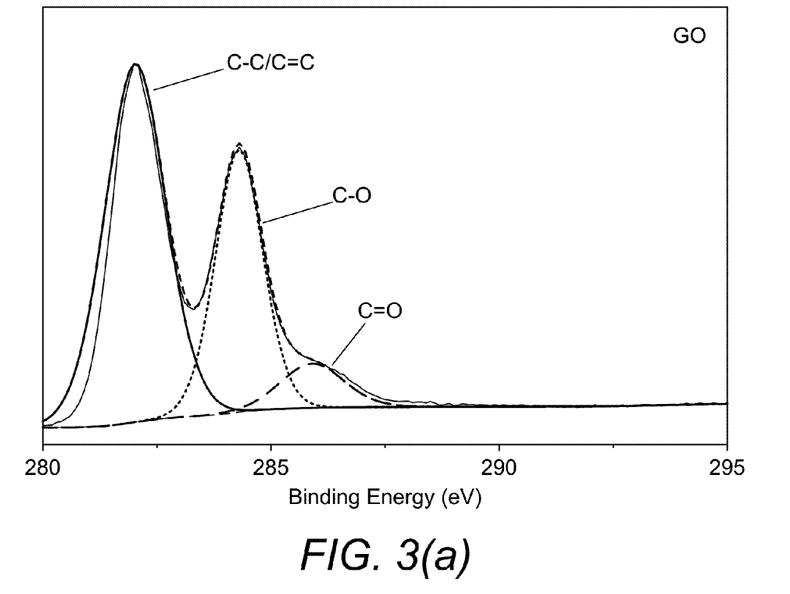
Figure 3B:
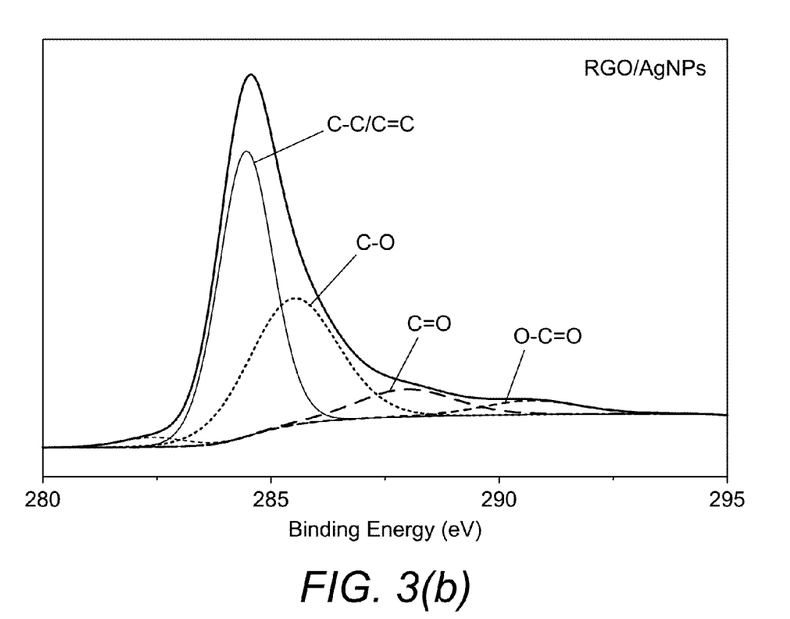
Figure 3C:
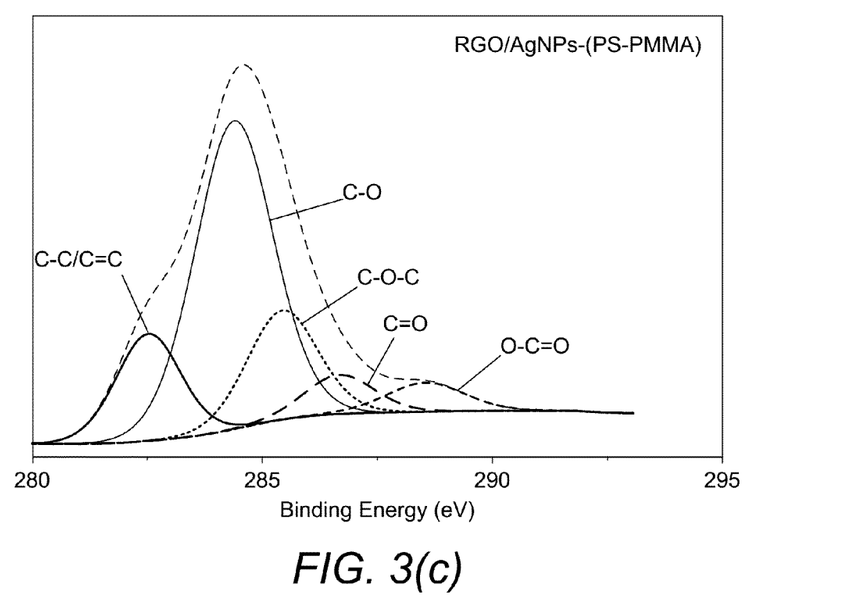
Figure 3D:
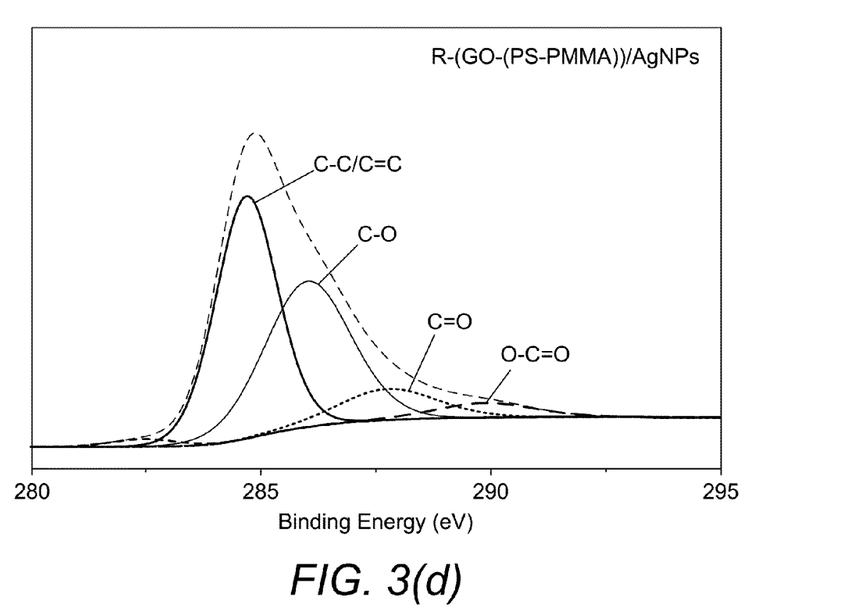
Figure 3E:
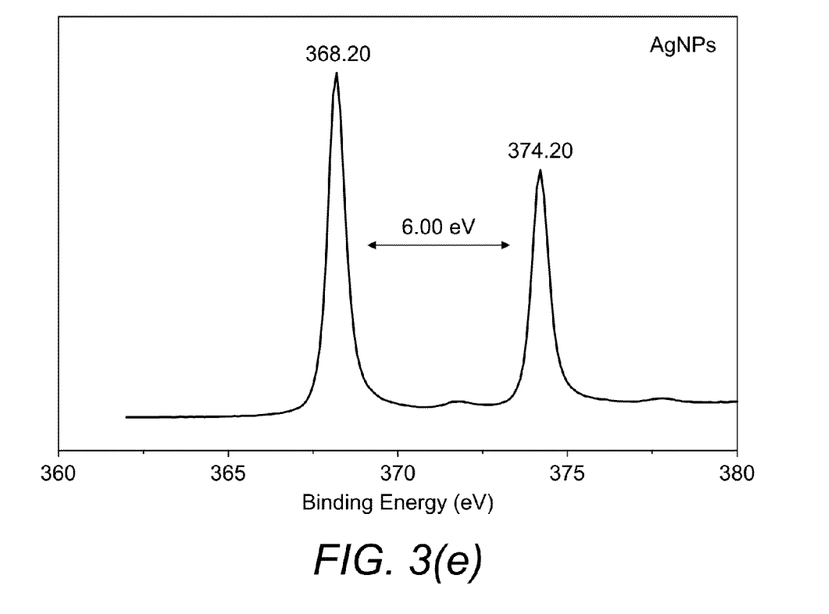
Figure 3F:
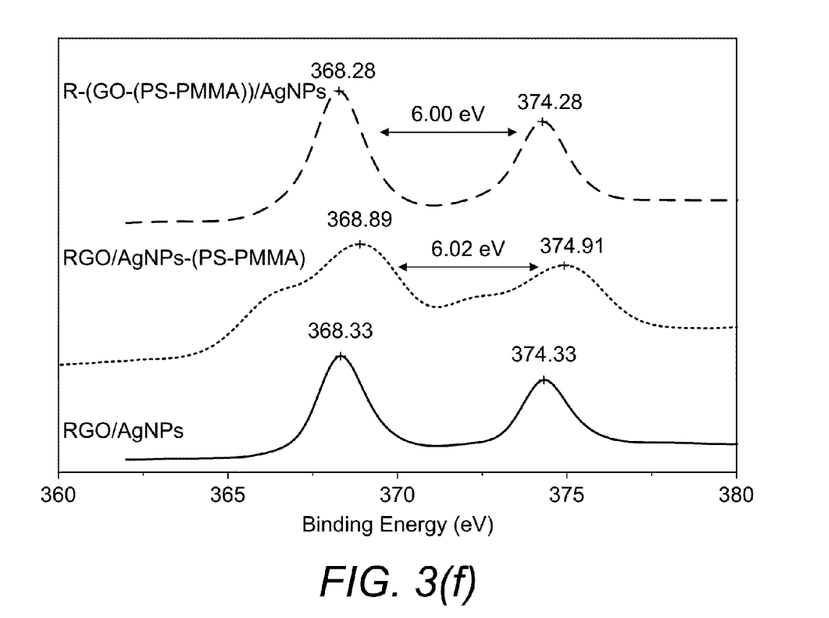

XRD analyses of the RGO/AgNPs/PS-PMMA composites were performed. FIG. 2 displays the XRD patterns for AgNPs, RGO/AgNPs, RGO/AgNPs-(PS-PMMA), and R-(GO-(PS-PMMA))/AgNPs nanocomposite. The crystalline XRD pattern of the AgNPs (a) exhibits a peaks at 28 values of approximately 38.1°, 44.4°, 64.5°, and 77.5°, which correspond to (111), (200), (220), and (311), and indicate the formation of metallic silver (Ag) with face-centered cubic (fcc) symmetry (JCPDS No. 00-003-0921). For RGO/AgNPs-(PS-PMMA) nanocomposite (c), it is difficult to find the AgNPs in the XRD pattern, which might suggest that the AgNPs are intercalated within the RGO/(PS-PMMA) composites. In the case of R-(GO-(PS-PMMA))/AgNPs nanocomposite (d), the XRD pattern shows the diffraction peaks of metallic Ag, and disappearing of GO and RGO peaks, conforming the formation of AgNPs and the reduction of GO, and hence the exfoliation of RGO/AgNPs sheets within the copolymer matrix. The intensity and broadening of peaks reflects the high degree of crystallinity and related to smaller particle size of the AgNPs.

The chemical changes and the formation of AgNPs on the surface of nanocomposite were further studied using XPS, and the results are summarized in FIG. 3. The C1s XPS spectra of GO (FIG. 3a) exhibits the typical peaks at 282.0, 284.3, and 285.9 eV, which correspond to C—C, C—O, and C (epoxy/alkoxy), respectively. The less intense peaks corresponding to the oxygenated functionalities in FIGS. 3b-d compared to FIG. 3a confirms the successful reduction of GO into RGO within the PS-PMMA matrix in the presence of hydrazine hydrate via the MWI method. Furthermore, XPS study confirmed the success of the metallic AgNPs formation within the composites. FIGS. 3e and 3f show the extent of two binding energies for Ag3d for the metallic AgNPs at 374.20 and 368.20 eV corresponding to Ag3d$_{3/2}$ and Ag3d$_{5/2}$ respectively which indicate the metallic nature of silver. In case of R-(GO-(PS-PMMA))/AgNPs (FIG. 3f), the XPS spectra shows the splitting of the 3d duplet is 6.00 eV. However, the splitting of 3d doublet in the composites which was prepared without MWI is 6.02 eV. This negative shift (−0.02 eV) may indicate that the stronger interaction may be due to MWI, which enhanced the electron transfer from the electron-rich RGO/PS-PMMA composites to AgNPs (J. Li et. al. 2012).

Figure 4:
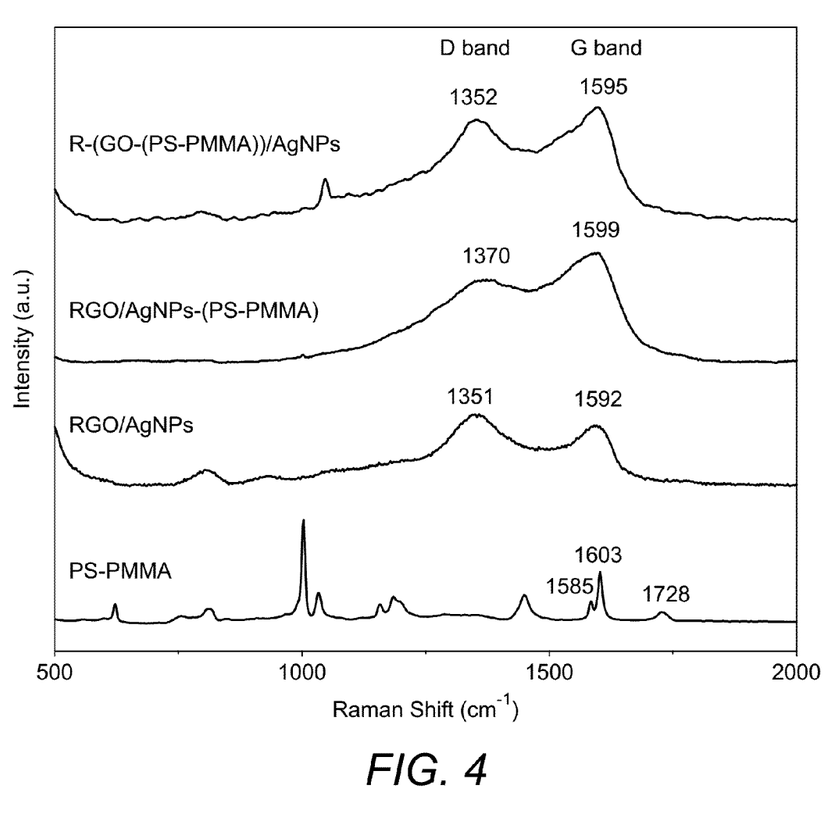
FIG. 4. Raman spectra of RGO/AgNPs/(PS-PMMA) nanocomposite.

Raman spectroscopy was also employed to characterize the RGO/AgNPs/PS-PMMA nanocomposite. Raman spectroscopy is a very powerful tool that provides essential information for evaluating the covalent modification of RGO nanosheets (P. Zhang et. al. 2011). Raman spectra (FIG. 4) show that the major scattering peaks of PS and PMMA were observed. The observed peaks at 1603 and 1585 cm$^{-1}$, and 1728 cm$^{-1}$ due to stretching of phenyl, and C=O groups for PS and PMMA, respectively. A comparison of the intensity of the characteristic D band at −1350 cm$^{-1}$ and the G band at −1595 cm$^{-1}$ is a well-accepted method for estimating the quality and structural order of graphitic structures. The D band is related to the sp$^3$ states of carbon and is used as proof of disruption in the aromatic π-electron system in RGO. In addition, the G band is related to the sp$^2$ state of carbon. The intensity of the D-band reflects the density of defects in the composites which may be caused by thermal exfoliation, the presence of oxygen-containing groups or graphene-metal interactions (Gutes et. al. 2012). In this work, ratios of the intensities of D/G ($I_D/I_G$) of RGO/AgNPs, RGO/AgNPs-(PS-PMMA), and R-(GO-(PS-PMMA))/AgNPs are 1.46, 1.09 and 1.33, respectively, reflecting an increase in defect as a result of the interaction between the n-network of RGO/AgNPs within phenyl and acrylate groups of PS-PMMA polymer matrix. The results clearly indicate an increase in the intensity of the ($I_D/I_G$) band in case of MWI nanocomposite in comparison when the MWI was not used. This result indicates that the sp$^2$-hybridized carbons were converted to sp$^3$ hybridized carbons, which may be due to the covalent attachment of RGO/AgNPs within the PS-PMMA polymer matrix (Fang et. al. 2009). Moreover, these peaks are shifted to lower wavenumbers (~1352 and ~1595 cm$^{-1}$), which is might be due to the stronger, defect induced, and covalent attachment of the PS-PMMA chains onto the surface of RGO/AgNPs. This shows that R-(GO-(PS-PMMA))/AgNPs nanocomposite prepared by MWI are more efficient to make covalent interaction than that of in situ method.

Figure 5:
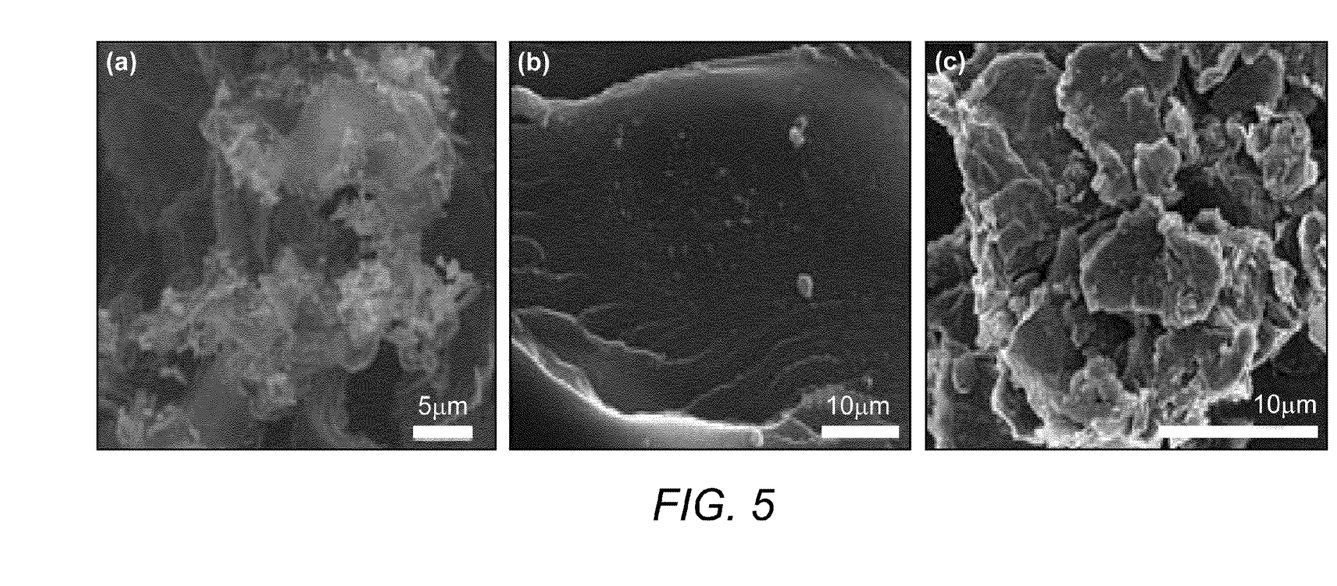
FIG. 5. (a), (b), (c), The SEM images of (a) RGO/AgNPs, (b) RGO/AgNPs-(PS-PMMA), and (c) R-(GO-(PS-PMMA))/AgNPs nanocomposite.

The morphology of the RGO/AgNPs/(PS-PMMA) nanocomposite was studied by SEM as displayed in FIG. 5. The SEM image of RGO/AgNPs (FIG. 5 section a) shows that the AgNPs were observed at the surface and imbedded within RGO sheets; with good dispersion. The SEM image of RGO/AgNPs-(PS-PMMA) nanocomposite (FIG. 5 section b) shows that the wrinkled and crumpled profiles of RGO/AgNPs were dispersed within the PS-PMMA matrix. In the case of R-(GO-(PS-PMMA))/AgNPs nanocomposite (FIG. 5 section c), the AgNPs (white spots) were anchored and well dispersed within PS-PMMA matrix.

Figure 6:
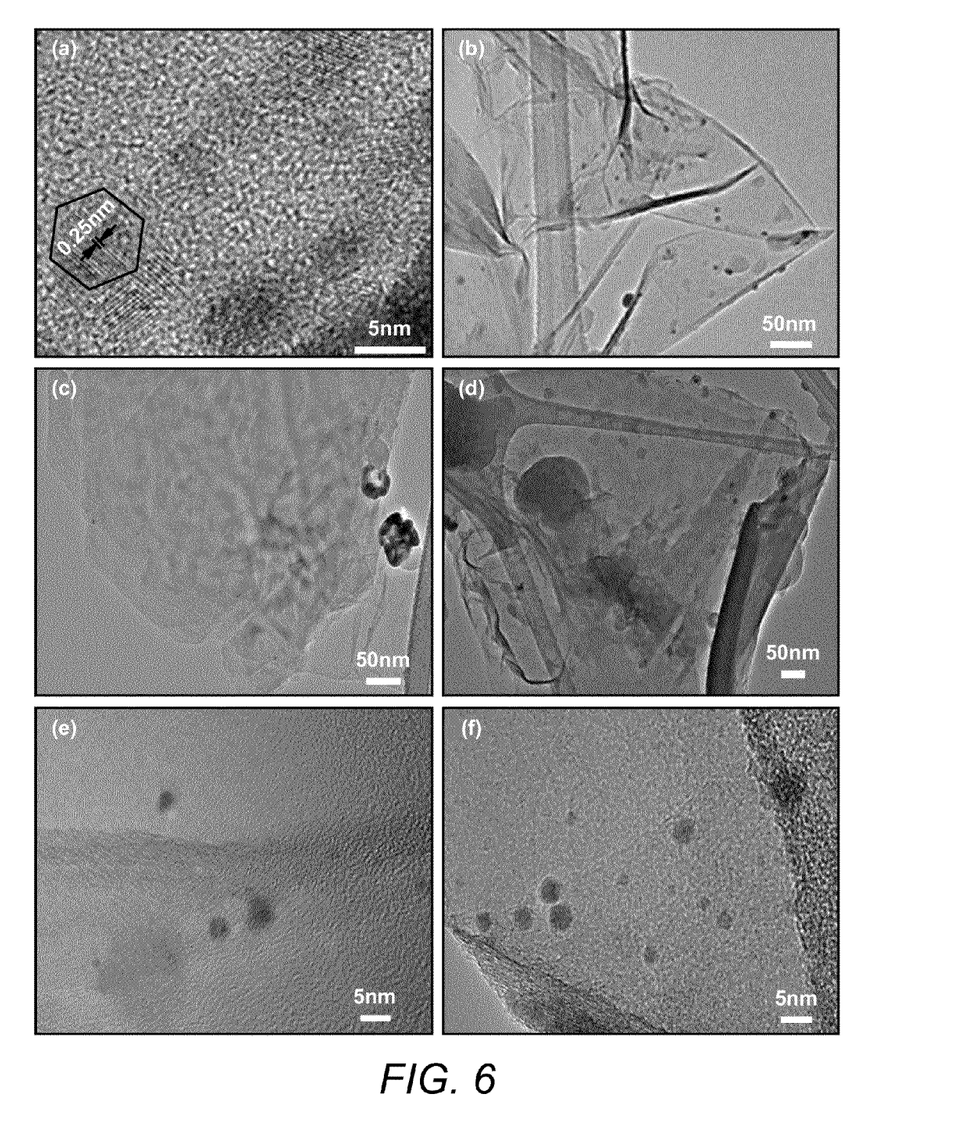
FIG. 6. (a), (b), (c), (d), (f) The HRTEM images of (a) AgNPs, (b) RGO/AgNPs, (c, e) RGO/AgNPs-(PS-PMMA), and (d, f) R-(GO-(PS-PMMA))/AgNPs nanocomposite.

The morphology of the nanocomposite and formation of AgNPs were further studied by using HRTEM as displayed in FIG. 6. HRTEM image of AgNPs (FIG. 6 section a) shows uniform dispersion with some agglomeration of smaller particles. A slightly distorted, hexagon-shaped AgNPs with the measured lattice spacing of 0.25 nm indicates that these AgNPs preserved the growth of the (fcc) cubic symmetry crystal plan (J. Shen et. al. 2010). The HRTEM image of RGO/AgNPs (FIG. 6 section b) shows that AgNPs are dispersed within the interface regions of exfoliated RGO sheets, indicating strong interaction between RGO and AgNPs. Note that RGO/AgNPs nanosheets are weakly dispersed within PS-PMMA matrix (FIG. 6 sections c, and e). However, when the MWI were used R-(GO-(PS-PMMA))/AgNPs (FIG. 6 sections d, and f), the images clearly show that RGO/AgNPs are well dispersed within PS-PMMA matrix. The XRD, SEM and HRTEM results confirmed that AgNPs were successfully formed and dispersed within RGO/PS-PMMA composites. This result may be attributed to some interactions between the RGO nanosheets, AgNPs, and PS-PMMA polymer matrix. The uniformly dispersion of AgNPs within the exfoliated RGO and PS-PMMA matrix were enhanced and improved by MWI, which should enhance the thermal properties of the nanocomposite.

Figure 7:
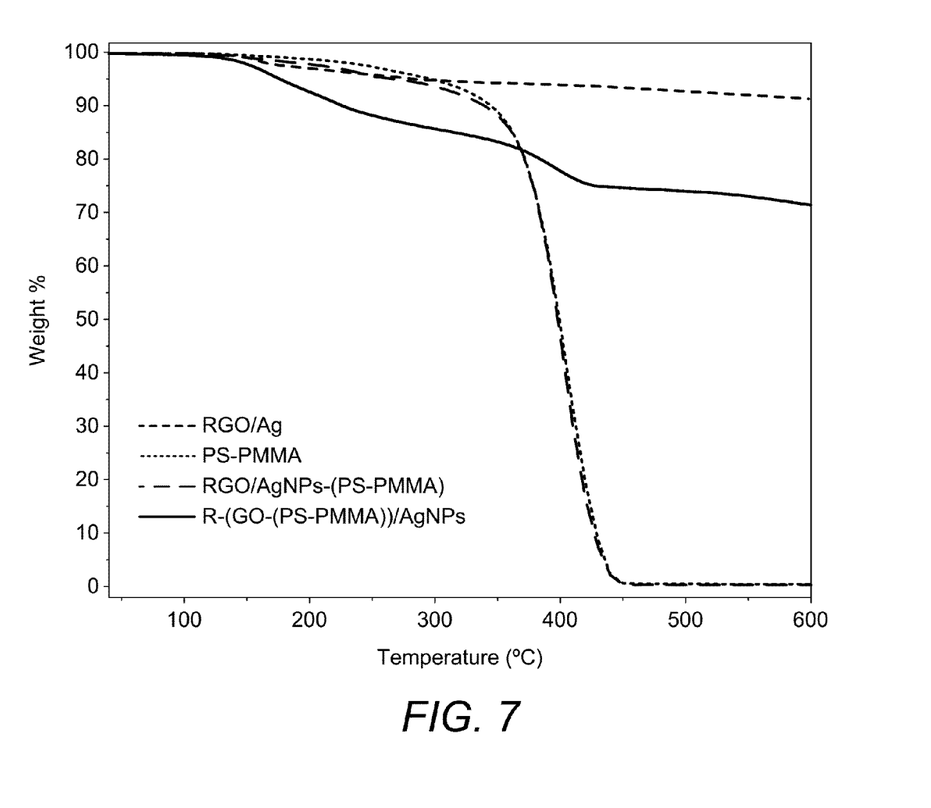
FIG. 7. TGA thermograms of RGO/AgNPs/(PS-PMMA) nanocomposite prepared via in situ and MWI method.

Thermal gravimetric analyses (TGA) were used to investigate the thermal stability and interfacial interaction between RGO/AgNPs and the PS-PMMA matrix. Interestingly, for R-(GO-(PS-PMMA))/AgNPs, the thermogram (FIG. 7) clearly indicates a strong enhancement in the thermal stability compared to neat PS-PMMA, and RGO/AgNPs-(PS-PMMA) (FIG. 7, Table 1). We attributed this result to the homogenous dispersion and random alignment of the RGO/

AgNPs filler within the PS-PMMA matrix. Therefore, incorporation of RGO/AgNPs via MWI can improve the thermal stability of the composites. In MWI, dielectric heating energy is transferred directly to the reactants, and the energy is supplied to the molecules faster than they are able to relax creating high instantaneous temperatures that increase the yield and quality of the product, which is in agreement with the results from our study. Therefore, our approach is promising for the development of a new class of RGO/MNPs-polymer composites.

To understand the MWI effect on the thermal behavior and on the dispersion of RGO/AgNPs within PS-PMMA composites, Differential Scanning calorimetry (DSC) of neat PS-PMMA, RGO/AgNPs-(PS-PMMA), and R-(GO-(PS-PMMA))/AgNPs nanocomposite were performed and the results are shown in (FIG. 8) and summarized in Table 1.

Table 1: Summary of the thermal behavior data obtained from TGA and DSC measurements.

| Sample | $T_{deg}^a$ (° C.) | $T_d^b$ (° C.) | $T_{max}^c$ (° C.) | $T_g$ (° C.) |
|---|---|---|---|---|
| RGO/AgNPs | 158 | — | — | — |
| PS-MMA | 288,367 | 344 | 397 | 93.5 |
| RGO/AgNPs-(PS-PMMA) | 400 | 340 | 397 | 88.0 |
| R-(GO-(PS-PMMA))/AgNPs | 196,400 | 228 | <800 | 181.0 |

$^a$The degradation temperature obtained from the Dr'Iti (derivative thermogram) in the decomposition stage.
$^b$The degradation temperature at a 10% weight loss in the decomposition stage.
$^c$The maximum degradation temperature at a 50% weight loss in the decomposition stage.

Figure 8:
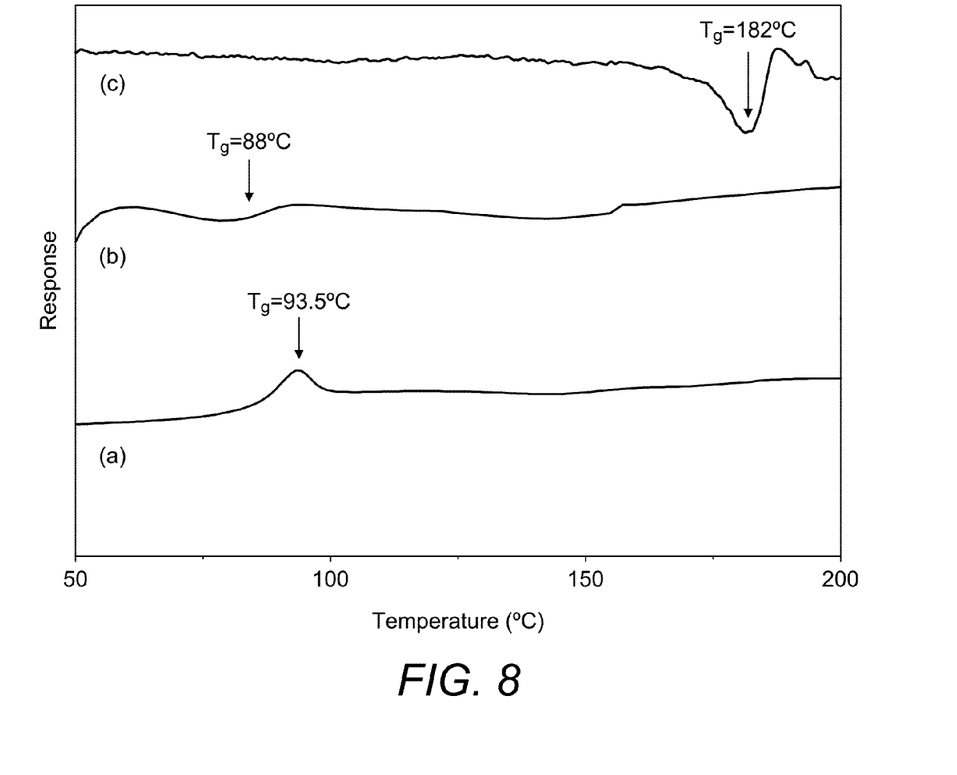
FIG. 8. TGA thermograms of (a) neat PS-PMMA (b) RGO/AgNPs-(PS-PMMA) and (c) R-(GO-(PS-PMMA))/AgNPs nanocomposite.

For the RGO/AgNPs-(PS-PMMA) nanocomposite, the thermogram shows that the $T_g$ value of the nanocomposite ($T_g$=88° C.) decreased by 5.5° C. compared to the neat PS-PMMA ($T_g$=93.5° C.) (FIG. 8). In the case of R-(GO-(PS-PMMA))/AgNPs, the curve shows a significantly improved thermal stability, with a $T_g$ of 182° C., which is 88.5° C. higher than that of the neat PS-PMMA. This result suggests a very strong interaction between the PS-PMMA chains and RGO/AgNPs. Our approach to intercalate the RGO/AgNPs within the PS-PMMA matrix using MWI method, clearly enhance the thermal properties of the nanocomposite. Previous work has shown that the interfacial strength between nanofillers and polymers and consequently, the thermal properties of nanocomposite, can be altered by varying the sample preparation method. In this work, the $T_g$ shift may be attributed to the presence of so called 'interphase' polymer networking, which arises due to the interaction of the chains with the RGO/AgNPs surfaces surface, which may restricted the mobility, creating an enormous volume of matrix polymer. Percolation of this network of interphase polymer could then manifest the large $T_g$ shift of the polymer composite (Huang et. al. 2011, S. Yej Feng 2013). Therefore, good dispersion without agglomeration of RGO/AgNPs may result from the fast thermal reduction process that is offered by MWI.

In conclusion, we report a novel in situ method for incorporation of RGO/AgNPs within a polymer matrix by the in situ bulk polymerization using MWI. The results indicate that the obtained nanocomposite prepared using MWI exhibited a better morphology and dispersion with enhanced thermal stability compared to the nanocomposite prepared without MWI.

Figure 9:
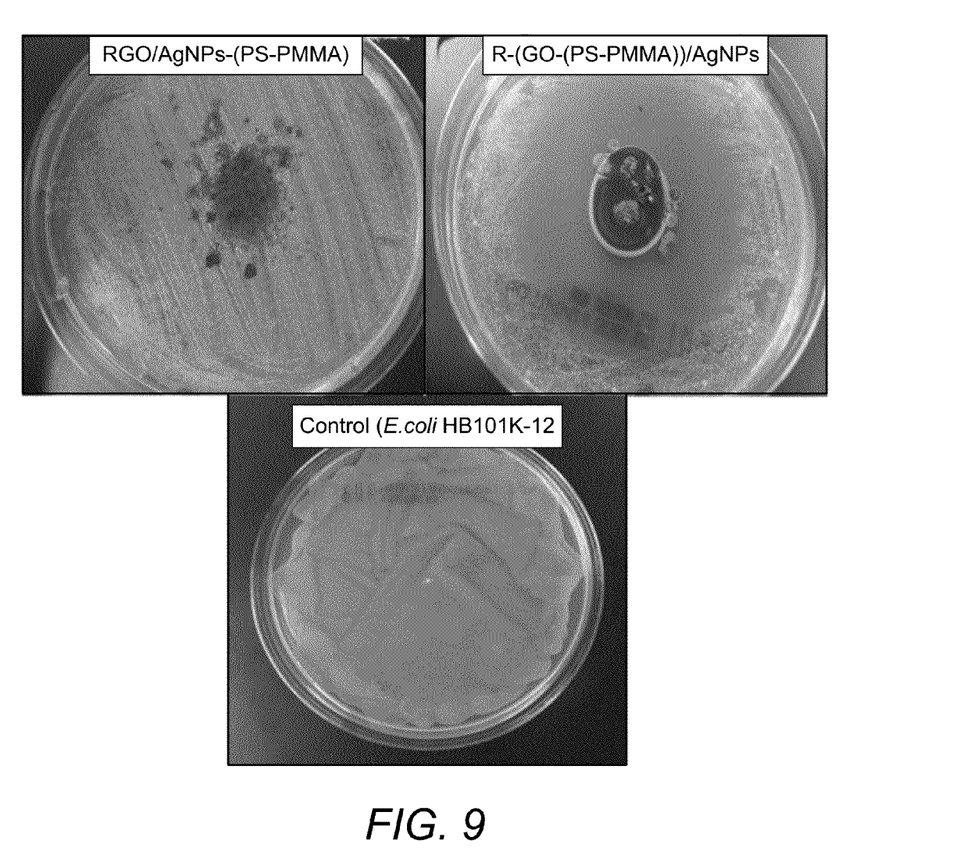
FIG. 9. shows the antibacterial activity of RGO/AgNPs-(PS-PMMA) and R-(GO-(PS-PMMA))/AgNPs nanocomposite against *E. coli* HB 101 K-12.

FIG. 9 shows the antibacterial activity of RGO/AgNPs-(PS-PMMA) and R-(GO-(PS-PMMA))/AgNPs nanocomposites against *E. coli* HB 101 K-12, which was compared by using the diameter inhibition zone (DIZ) in disk diffusion test. The (DIZ) reflects the magnitude of microorganism sensitivity. The microorganism that is sensitive to tested samples shows larger DIZ compare with smaller or no DIZ for resistant microorganism (Zhang et. al. 2011)

For RGO/AgNPs-(PS-PMMA) nanocomposites (FIG. 9), the image shows a weak inhibition with 3 mm inhibition zone. On other hand, R-(GO-(PS-PMMA))/AgNPs nanocomposites, shows a strong inhibition zone with 27 mm, which indicates toxicity against *E. coli*. This result indicates that the nanocomposites prepared by MWI shows strong activity against the tested microbial strains compare to that obtained without MWI, which might be due to damaging proteins and genetic material and hence might causing cell death or stop bacterial growing.

In addition, it will be appreciated that the various composition of the nanocomposite and method of making the nanocomposite disclosed herein may be embodied using means for achieving the various combinations of material and irradiation doses using microwave. Accordingly, the specification and drawings are to be regarded in an illustrative rather than a restrictive sense.

What is claimed is:

1. An antimicrobial nanocomposite composition comprising polymerizing, by in-situ radical bulk polymerization, a first mixture of a styrene, a methyl methacrylate, and a graphene oxide; wherein the styrene and methyl methacrylate are present at a specific weight ratio of 1:1 and graphene oxide is present at 2.0 weight percent based on the weight of the styrene and methyl methacrylate, to obtain a graphene oxide polystyrene-polymethyl methacrylate (GO/PS-PMMA) composite; mixing the GO/PS-PMMA composite with hydrazine hydrate solution and a silver nitrate to form a second mixture; and treating the second mixture with microwave irradiation to obtain a reduced graphene oxide polystyrene-polymethyl methacrylate silver nanoparticle composite (R-(GO)-(PS-PMMA))AgNPs).

2. A medical device comprising the R-(GO-(PS-PMMA)) AgNPs antimicrobial nanocomposite composition of claim 1.

3. The medical device of claim 2, wherein the medical device is at least one of a denture, bone cement and tube.

4. An article comprising the R-(GO-(PS-PMMA))AgNPs antimicrobial nanocomposite composition of claim 1.

5. The article of claim 4, wherein the article is at least one of a paper, automotive and paint.

* * * * *